United States Patent [19]

Samson et al.

[11] Patent Number: 5,782,811
[45] Date of Patent: Jul. 21, 1998

[54] KINK-RESISTANT BRAIDED CATHETER WITH DISTAL SIDE HOLES

[75] Inventors: Gene Samson, Milpitas; Hanh Doan, Santa Clara, both of Calif.

[73] Assignee: Target Therapeutics, Inc., Fremont, Calif.

[21] Appl. No.: 652,701

[22] Filed: May 30, 1996

[51] Int. Cl.⁶ .................................................. A61M 25/00
[52] U.S. Cl. .................................. 604/282; 604/280
[58] Field of Search .................................. 604/264, 281, 604/282, 280

[56] References Cited

U.S. PATENT DOCUMENTS

| | | |
|---|---|---|
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,721,231 | 3/1973 | Hubert . |
| 3,753,700 | 8/1973 | Harrison et al. . |
| 3,841,308 | 10/1974 | Tate . |
| 3,924,632 | 12/1975 | Cook . |
| 3,938,529 | 2/1976 | Gibbons . |
| 4,279,252 | 7/1981 | Martin . |
| 4,425,919 | 1/1984 | Alston, Jr. et al. . |
| 4,484,586 | 11/1984 | McMickle et al. . |
| 4,516,972 | 5/1985 | Samson . |
| 4,639,252 | 1/1987 | Kelly et al. . |
| 4,661,094 | 4/1987 | Simpson . |
| 4,739,768 | 4/1988 | Engelson . |
| 4,801,297 | 1/1989 | Mueller . |
| 4,806,182 | 2/1989 | Rydell et al. . |
| 4,832,681 | 5/1989 | Lenck . |
| 4,863,441 | 9/1989 | Lindsay et al. . |
| 4,981,478 | 1/1991 | Evard et al. . |
| 5,021,044 | 6/1991 | Sharkawy . |
| 5,037,404 | 8/1991 | Gold et al. . |
| 5,057,092 | 10/1991 | Webster, Jr. . |
| 5,061,257 | 10/1991 | Martinez et al. . |
| 5,147,334 | 9/1992 | Moss . |
| 5,176,660 | 1/1993 | Truckai . |
| 5,201,723 | 4/1993 | Quinn . |
| 5,217,482 | 6/1993 | Keith . |
| 5,248,305 | 9/1993 | Zdrahala . |
| 5,256,141 | 10/1993 | Gencheff et al. . |
| 5,275,152 | 1/1994 | Krauter et al. ............... 604/282 |
| 5,336,205 | 8/1994 | Zenzen et al. . |
| 5,380,307 | 1/1995 | Chee et al. . |
| 5,454,795 | 10/1995 | Samson . |
| 5,472,435 | 12/1995 | Sutton . |
| 5,496,294 | 3/1996 | Hergenrother et al. ............ 604/282 |
| 5,509,910 | 4/1996 | Lunn ............................... 604/282 |
| 5,522,832 | 6/1996 | Kugo et al. .................... 604/282 |
| 5,569,197 | 10/1996 | Helmus et al. ................... 604/282 |
| 5,601,539 | 2/1997 | Corso, Jr. ....................... 604/282 |

*Primary Examiner*—Michael Powell Buiz
*Assistant Examiner*—Ronald K. Stright, Jr.
*Attorney, Agent, or Firm*—Morrison & Foerster

[57] ABSTRACT

This is a catheter section having a number of radially placed holes through the catheter section wall and a catheter assembly including that section. That catheter assembly may be used in accessing and treating a tissue target within the body, typically one which is accessible through the vascular system. Central to the catheter section is the presence of a braided metallic reinforcing member, typically of super-elastic alloy ribbon, situated in such a way to provide an exceptionally thin wall, controlled stiffness, high resistance to kinking, and complete recovery in vivo from kinking situations. The orifices in the section are optimally placed in the interstices between the turns of the braid. The braid may have a single pitch or may vary in pitch along the axis of the catheter or catheter section. The braided ribbon reinforcing member typically is placed between a flexible outer tubing member and an inner tubing member to produce a catheter section which is very flexible but highly kink resistant. The catheter sections made according to this invention may be used alone or in conjunction with other catheter sections either made using the concepts shown herein or made in other ways. The more proximal sections of the catheter assembly are often substantially stiffer than the more distal sections due to the presence of stiff polymeric tubing or metallic tubing or composited materials in the stiffer section.

27 Claims, 8 Drawing Sheets

KINK-RESISTANT BRAIDED CATHETER WITH DISTAL SIDE HOLES

FIELD OF THE INVENTION

This invention is a surgical device. In particular, it is a catheter section having a number of radially placed holes through the catheter section wall and a catheter assembly including that section. That catheter assembly may be used in accessing and treating a tissue target within the body, typically one which is accessible through the vascular system. Central to the invention is the use of a braided metallic reinforcing member in the catheter section, typically of super-elastic alloy ribbon, situated in such a way to provide an exceptionally thin wall, controlled stiffness, high resistance to kinking, and complete recovery in vivo from kinking situations. The orifices in the section are optimally placed in the interstices between the turns of the braid. The braid may have a single pitch or may vary in pitch along the axis of the catheter or catheter section. The braided ribbon reinforcing member typically is placed between a flexible outer tubing member and an inner tubing member to produce a catheter section which is very flexible but highly kink resistant.

The catheter sections made according to this invention may be used alone or in conjunction with other catheter sections either made using the concepts shown herein or made in other ways. The more proximal sections of the catheter assembly are often substantially stiffer than the more distal sections due to the presence of stiff polymeric tubing or metallic tubing or composited materials in the stiffer section.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of diseases of the circulatory system is via angioplasty (PCA). Such a procedure uses catheters having balloons on their distal tips. It is similarly common that those catheters are used to deliver a radio-opaque agent to the site in question prior to the PCA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered.

This invention is an adaptable one and may be used in a variety of catheter formats. The invention utilizes the concept of combining one or more polymeric tubes with a metallic braid comprising ribbons of a super-elastic alloy. The construction technique has the benefit of producing catheter sections having small overall diameters but with exceptional strength, resistance to kinking, and recovery from kinking (even in vivo) should such kinking occur. This catheter may be used in conjunction with a guidewire, but the catheter body may also be used as a flow-directed catheter with the attachment of a balloon or in combination with a specifically flexible tip, as is seen, for instance, in U.S. Pat. No. 5,336,205 to Zenzen et al., the entirety of which is incorporated by reference.

The use of braids in a catheter body is not a novel concept. Typical background patents are discussed below.

There are a number of catheters discussed in the literature which utilize catheter bodies having multiply-wrapped reinforcing material. These catheters include structures having braided bands or ones in which the spirally wound material is simply wound in one direction and the following layer or layers are wound in the other.

Krippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in some region other than in the body's periphery or in its soft tissues.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is a polyaramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal polymer fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

None of the documents cited above provides a structure required by the disclosure and claims recited below, particularly when the flexibility and ability to resist kinks is factored into the physical description of the devices.

SUMMARY OF THE INVENTION

This invention includes an infusion catheter section made up of an inner liner and an outer covering and having a super-elastic alloy ribbon braid located between the liner and the covering. Located generally in the interstices between adjacent turns of the braid ribbon are a number of infusion orifices. The inner liner may be of a polymeric composition. The inner liner and the outer covering, should they be adjacent the braid and both polymeric, may be selected from polymers which are melt-compatible or melt-miscible with each other. In this way, adjacent polymeric layers hold fast to the braid located between them. More preferably, the outer liner is selected such that it is adherent to the inner liner.

The super-elastic alloy braid is, in its most basic form, a braid comprising a number of small super-elastic alloy ribbons wound and treated in such a way that the resulting braid is dimensionally stable and the braided ribbons do not twist. The more basic forms of braids used in this invention include those which are made up of an even number of equally sized ribbons. Half of the ribbons are woven in a clockwise direction (as viewed along the axis of the braid) and the remaining half of the ribbons are woven in a counterclockwise direction. The various ribbons may, of course, be of differing size but the sum of the ribbons used in a particular direction should equal those wound in the other direction. Any imbalance will typically cause a helical curl in the resulting catheter. The super-elastic alloy of choice contains nickel and titanium and is known generically as nitinol. Nitinol is an alloy of nickel and titanium which is blended and heat treated in a specific way to produce an alloy having exceptional resistance to plastic deformation upon physical strain. In addition to nickel and titanium, preferred compositions of the alloy may contain a modest amount, up to about 5%, or up to about 8%, of an iron group metal. Especially desired are ternary alloys containing at least about 1.5% (wt) of one or more alloying members selected from the group consisting of vanadium, chromium, manganese, iron, and cobalt, and particularly chromium or iron. The catheter section may additionally have other various layers of polymeric covering and liners as well as metallic tubing members desirably of braid or helical coils. Especially preferred liners comprise polytetrafluoroethylene (TFE) polymer. Hydrophilic coatings both on the interior and exterior are additionally contemplated.

The kink resistance of the catheter section is due to the presence and composition of the braid in cooperation with the tightly held polymers. In addition to exceptional kink resistance, the catheter section may be made in such a way that the wall is extraordinarily thin, particularly when compared to walls of catheters having equal strength but made solely of polymeric materials. The catheter section additionally is very resilient in that, unlike virtually any other commercial catheter, should the catheter section be kinked, the kink is self-healing. This resiliency means that the catheter need not be withdrawn from a patient's vasculature simply because the catheter has inadvertently kinked. Simple movement of the catheter will cure the kink. Kinking minimization is a matter of concern with many catheters in the marketplace today.

This invention additionally includes catheter sections with braids having more than one pitch or diameter or braid density in a section. The stiffness of the catheter section may be varied continuously by continuously varying the pitch or in a stepwise fashion by stepwise varying the pitch. The pitch may be varied during production of the braid or by changing the diameter of the braid after production. The braid may be partially constructed of polymeric fibers or carbon fibers either replacing a portion of the metallic ribbons or polymeric materials or placed in conjunction with a ribbon in the braid. Other metals, e.g., noble metals such as members of the platinum group or gold, may be used in the braid itself in much the same way to impart radio-opacity to the braid. To tailor the stiffness of the braid, the braid may first wound and portions of the ribbon then removed.

The infusion catheter section of this invention may be used as a catheter assembly by itself—obviously in conjunction with such necessary and ancillary components as a Luerlock and some manner of providing radio-opacity to the catheter. The infusion catheter section of this invention may be used in nose-to-tail configuration with other catheter sections of similar configuration or with catheter sections made in some other fashion.

The infusion catheter section is typically the distal-most section of a catheter assembly. However, it may be used in a catheter assembly having at least a.) a more distal section made up preferably of an inner liner and an outer covering and having a super-elastic alloy braid located between the liner and interior to the outer covering and b.) a more proximal section comprising a stiff polymeric or metallic tubing member, possibly with an inner lubricious liner. Other sections of these or other designs may be placed variously between the noted sections or distal of the distal braided section noted above.

DESCRIPTION OF THE INVENTION

This invention includes a kink-resistant catheter section containing at least an inner liner and a flexible outer member having a super-elastic alloy, ribbon braid located between the inner and outer members. Located generally in the areas between adjacent turns of the braid ribbon are a number of infusion orifices. The invention includes catheters comprising at least one such catheter section, typically distally located. The catheter section is configured so that it desirably has a critical bend diameter of no more than about 3 mm., preferably no more than 2 mm., and most preferably no more than 1 mm. Desirably, the catheter section self-recovers at least 95% of its original "straightness" after it has been subjected to kinking.

Figure 1:
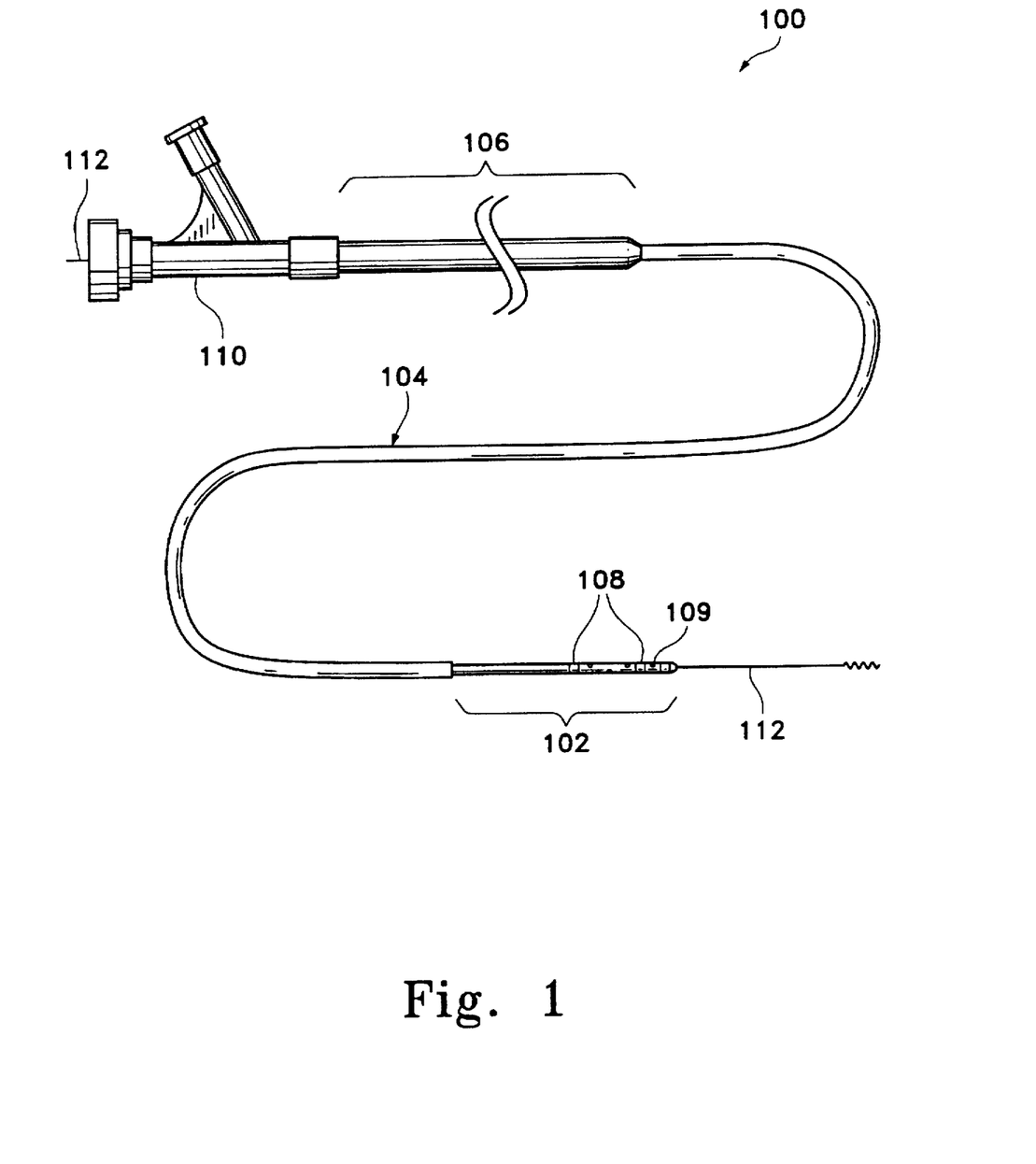
FIG. 1 shows, in side view, a typical three-section catheter made using the concepts of this invention.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever smaller vascular areas. This smaller diameter requires a concomitant thinning of the wall section. The thinner section walls may kink or ripple when actively pushed along the guidewire or when vasoocclusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration of the extraordinary convolutions of the neurological vasculature without trauma. Central to this invention is the presence of a kink resisting braid of the composition described below, in the distal section (102). That braid (not shown in this Figure) is situated with respect to the various orifices (109) such that the orifices (109) generally are between the turns of ribbon making up the braid. These orifices are used to infuse fluid treatments or diagnostic materials to the chosen site in the human body. Various known and often necessary accessories to the catheter assembly, e.g., one or more radio-opaque bands (108) at the distal region to allow viewing of the position of the distal region under fluoroscopy and a luer assembly (110) for guidewire (112) and fluids access, are also shown in FIG. 1.

The typical dimensions of this catheter are:

Overall length: 60–200 cm

Proximal Section (106): 60–150 cm

Intermediate Section (104): 20–50 cm

Distal Section (102): 2.5–30 cm

Obviously, these dimensions are not particularly critical to this invention and are selected as a function of the malady treated and its site within the body. Typical of the catheters made using this invention are those in the 2 French to 5 French range. The inner diameter of such catheters is then 10 mils to 42 mils.

Furthermore, a catheter made using this inventive concept need not be of three sections increasing stiffness as is shown in FIG. 1. The catheter may be of two discrete sections or may be of four or more discrete sections of differing flexibility. Through judicious choice of physical parameters for the catheter sections, the components may also have varying physical parameters (e.g., lubricity, flexibility, wall thickness, inner or outer layer member composition, etc.) within the sections.

Typically, although not necessarily, when a three section catheter is desired, the most proximal section (106) is the "more proximal" or "stiff" section described herein. Again, although not necessarily, when a three section catheter is desired, the most distal section (102) is the "more distal" or "least stiff" section. The mid section (104) may be braided and referred to as "more distal" if the situation warrants it. It is a rare infusion catheter that utilizes a more distal section which is stiffer than any of its more proximal sections.

An additional benefit of the invention is that the use of the super-elastic alloy braid permits the walls of the catheter to be comparatively thinner with no diminution of performance, e.g., crush strength or flexibility, and may provide an improvement in performance.

Figure 2:
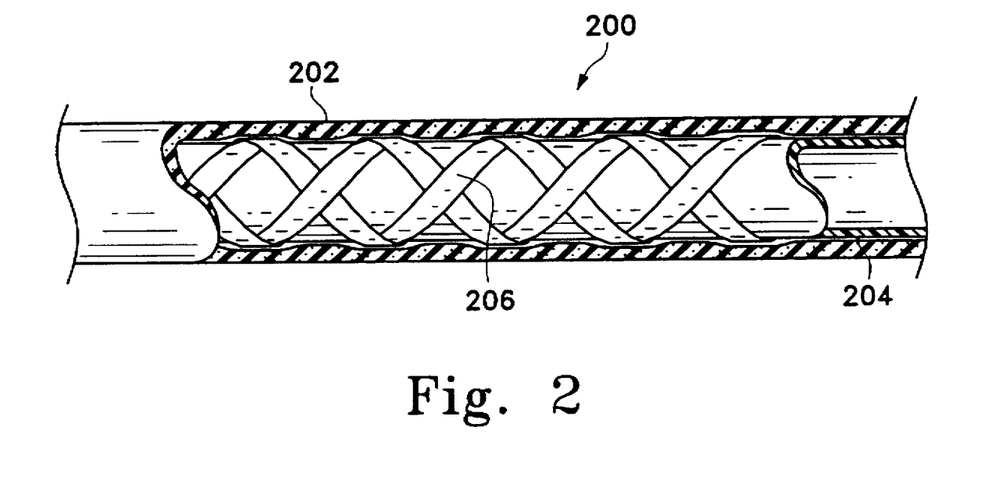
FIGS. 2, 3, and 4 show, in magnification, partial cross-sections of the inner portion of a catheter sections useful in this invention.

FIG. 2 shows a magnified partial cross-section of a catheter body or section (200) showing the most basic aspects of a braid-augmented catheter section. As shown there, the catheter body section has an outer covering member (202) and an inner liner member (204). Situated between outer member (202) and inner member (204) is braid member (206). As shown in FIG. 2, both outer member (202) and inner member (204) are polymeric. They may be of materials which tack to each other upon heating. They may also be melt-miscible. In some instances, they may contain adhesions or components which act in the manner of adhesives, but such is not necessary. Typically, for the simple variation shown in FIG. 2, the outer covering member (202) is of a material which is heatshrinkable (e.g., low density polyethylene) or may otherwise be coated onto the structure (e.g., polyurethanes) onto the inner member (204) and the braid (206). Preferred polymeric materials for the inner liner include polyethylene, polypropylene, polyvinyl chloride (PVC), ethyl vinyl acetate (EVA), polyurethanes, polyamides, polyethylene terephthalate (PET), and their mixtures and copolymers. Preferred materials further include the lubricious polymers such as fluoropolymers such as polytetrafluoroethylene (PTFE or TFE), ethylenechlorofluoroethylene (ECTFE), fluorinated ethylene propylene (FEP), polychlorotrifluoroethylene (PCTFE), polyvinylfluoride (PVF), or polyvinylidenefluoride (PVDF). Especially preferred is TFE.

We have found that when a fluorcarbon polymer is used as the inner tubing member, it is useful to etch the outside surface of the member to provide a good surface to which the adjacent polymers will adhere. Certain procedures using, for instance, aliphatic hydrocarbons and powdered sodium metal or powdered sodium metal and anhydrous ammonia or sodium metal in naphthalene/tetrahydrofuran or commercial etchants such as TETRA-ETCH sold by Gore & Associates as the etching solution are known to be effective in such service.

Another useful class of polymers are thermoplastic elastomers, including those containing polyesters as components. Typical of this class is HYTREL. Additionally, an adhesive may be coated onto the outer surface of the inner liner tubing. Polyesters and polyimides, in particular, are suitable as adhesives.

An outer covering of polyethylene or of EVA or their mixtures, copolymers, etc. are excellent choices for the outer covering member. The polymer to be used as the outer covering is typically extruded into a tubing of appropriate size and thickness and then cross-linked to raise the melt temperature of the resulting tubing. The tubing is then inflated and perhaps stretched to give the included polymer a specific molecular orientation. The tubing, so treated, may then be slipped over the combination of inner liner (204) and braid (206) and heat shrunk into place.

A variety of other polymers may be used, depending upon the use to which the catheter section is placed. For instance, if the section (200) is used as a proximal section, the outer tubing may be a polyimide, polyamides (such as the Nylons), high density polyethylene (HDPE), polypropylene, polyvinylchloride, various fluorocarbon polymers (for instance: PTFE, FEP, vinylidene fluoride, their mixtures, alloys, copolymers, block copolymers, etc.), polysulfones, or the like. Blends, alloys, mixtures, copolymers and block copolymers of these materials are also suitable if desired.

If a more flexible section is required, the outer tubing member (202) may also be of a member selected from a more flexible material such as polyurethanes, low density polyethylene (LDPE), polyvinylchloride, THV, etc. and other polymers of suitable softness or a modulus of elasticity. For the most-preferred variation of this invention, polyurethanes are desirable.

FIG. 2 shows the results of a heat-shrinking the outer tubing member (202) onto the assembly of inner liner tube (204) and braid (206). Contact regions between the outer covering member (202) and inner liner member (204) are shown in the interstices between the open weave of the braid (206). Although the open area between turns of the braid is not absolutely necessary as a means of allowing contact between the inner liner (204) and the outer covering (202), such is quite desirable. Furthermore, when the outer covering member (202) is placed on the outer surface of the catheter section (200) by dipping the inner assembly of braid (206) and inner member (204) into a molten or latex liquid, the contact is inevitable.

We have found that when using polyurethane as either the outer covering member (202) per se or as an inner portion of the outer covering member (202) (e.g., beneath a polyethylene layer), a suitable method for applying the polyurethane to the braid entails placement of a polyurethane tubing over the braid, placement of a polyethylene "shrinkwrappable" tubing over the polyurethane tubing, and heating the combination to pull the polyurethane down to the braid surface using the polyethylene tubing as the mover. The polyethylene may be removed or left in place.

The wall thickness of the outer tubing member (202) may be as thin as 0.5 mils, and as thick as 10 mils., depending upon catheter usage, section of the catheter chosen, polymer choice, and style of catheter.

Typically, a wall thickness of the inner liner (204) will be between 0.5 and 3.0 mils. These dimensions are obviously only ranges and each catheter variation must be carefully designed for the specific purpose to which it is placed.

Each of the polymers noted herein may be used in conjunction with radio-opaque filler materials such as barium sulfate, bismuth trioxide, bismuth carbonate, powdered tungsten, powdered tantalum, or the like so that the location of various portions of the catheter sections may be radiographically visualized within the human body.

As will be discussed below, it is within the scope of this invention to have multiple polymeric layers exterior of the braid (206) as well as multiple polymeric liner members interior to braid (206). Furthermore, it is within the scope of the invention to include multiple braids and/or flat ribbon coils between or amongst the various polymeric layers.

It is also within the scope of this invention to coat at least one of the exterior surface of outer member (202) and the inner surface of inner liner (204) with a lubricious layer, which either is chemically bonded to the layer or is physically coated on the relevant surface. A description of suitable procedures for producing such lubricious coatings is found at U.S. patent application Nos. 08/060,401 ("LUBRICIOUS CATHETERS"), filed May 12, 1993; 08/235,840 ("METHOD FOR PRODUCING LUBRICIOUS CATHETERS"), filed Apr. 29, 1995; and 08/272,209 ("LUBRICIOUS FLOW DIRECTED CATHETER"), filed Jul. 8, 1994, the entirety of which are incorporated by notice.

The metallic braid (206) shown in FIG. 2 is made up of a number of metallic ribbons. A majority of the metallic ribbons in braid (206) are of a member of a class of alloys known as super-elastic alloys.

Preferred super-elastic alloys include the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Commercial alloys containing up to about 5% or up to about 8% or more, of one or more other members of the iron group, e.g., Fe, Cr, Co, are considered to be encompassed within the class of super-elastic Ni/Ti alloys suitable for this service. Most preferred are alloys containing 1.5–2.5% Cr and having a transition temperature of less than 0° C.

When using a super-elastic alloy, an additional step may be desirable to preserve the shape of the stiffening braid. For instance, with a Cr-containing Ni/Ti super-elastic alloy which has been rolled into a 1×4 mil ribbon and formed into a 16-member braid, some heat treatment is desirable. Braids which are not treated in this way may unravel during subsequent handling or may undertake changes in diameter or braid member spacing during that handling. In any event, the braid is placed onto a mandrel, usually metallic, of an appropriate size. The braid is then heated to a temperature of 650 °–750° F. for a few minutes, possibly (but not necessarily) annealing the constituent ribbon. After heat treatment, the braid retains its shape and the alloy retains its super-elastic properties.

Metallic ribbons (202 and 206) that are suitable for use in this invention are desirably between 0.25 mil and 3.5 mil in thickness and 2.5 mil and 12.0 mil in width. By the term "ribbon", we intend to include elongated shapes, the cross-section of which are not square or round and may typically be rectangular, oval or semi-oval. They should have an aspect ratio of at least 0.5 (thickness/width). In any event, for super-elastic alloys, particularly nitinol, the thickness and width may be at the lower end of the range, e.g., down to 0.30 mil and 1.0 mil, respectively. Currently available ribbons include sizes of 0.75 mil×4mil, 1 mil×3 mil, 1 mil×4 mil, 2 mil×6 mil, and 2 mil×8 mil.

The ribbons making up the braid (206) shown in FIG. 2 may also contain a minor amount of non-super-elastic alloy materials. Although metallic ribbons are preferred as the ancillary materials because of their strength-to-weight ratios, fibrous materials (both synthetic and natural) may also be used. Preferred, because of cost, strength, and ready availability are stainless steels (SS304, SS306, SS308, SS316, SS318, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radio-opacity.

Suitable non-metallic ribbons include high performance materials such as those made of polyaramids (e.g., KEVLAR) and carbon fibers.

The braids utilized in this invention may be made using commercially available tubular braiders. The term "braid" is meant to include tubular constructions in which the ribbons making up the construction are woven radially in an in-and-out fashion as they cross to form a tubular member defining a single lumen. The braids may be made up of a suitable number of ribbons, typically six or more. Ease of production on a commercial braider typically results in braids having eight or sixteen ribbons.

The braid shown in FIG. 2 has a nominal pitch angle of 45°. Clearly the invention is not so limited. Other braid angles from 20° to 60° are also suitable. An important variation of this invention is the ability to vary the pitch angle of the braid either at the time the braid is woven or at the time the braid is included in the catheter section or sections.

Figure 3:
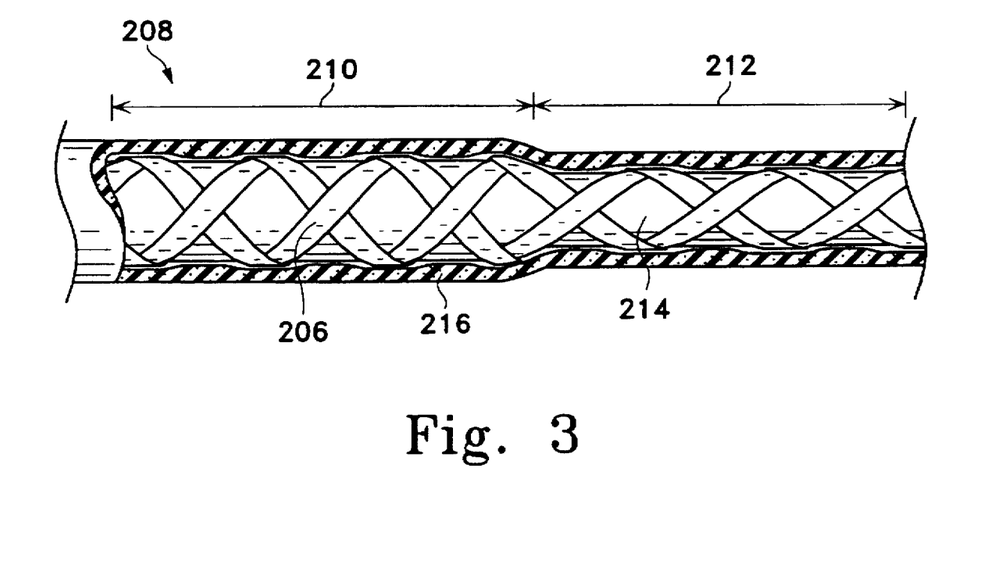

FIG. 3 shows a variation of a braid-augmented catheter section in which the braid (206) is used in a catheter section (208) having two portions of different diameter. The larger diameter portion (210) utilizes the braid with a nominal braid angle of 45 degrees and a smaller diameter portion (212) in which the same braid has a braid angle of 30 degrees. This diminution in catheter diameter may be accomplished in a number of different ways. For instance, inner liner (214) may be sized with two different diameters in the respected different portions (210 and 212) of the catheter section. The braid (206) may then be stretched axially as it is placed upon that liner. When the outer covering (216) is placed on the braid (206), the braid (206) will retain its multi-diameter configuration. This variation has the benefit of being quite simple in construction and yet provides a variety of different flexibilities to the catheter section without a significant change in the materials of construction.

Figure 4:
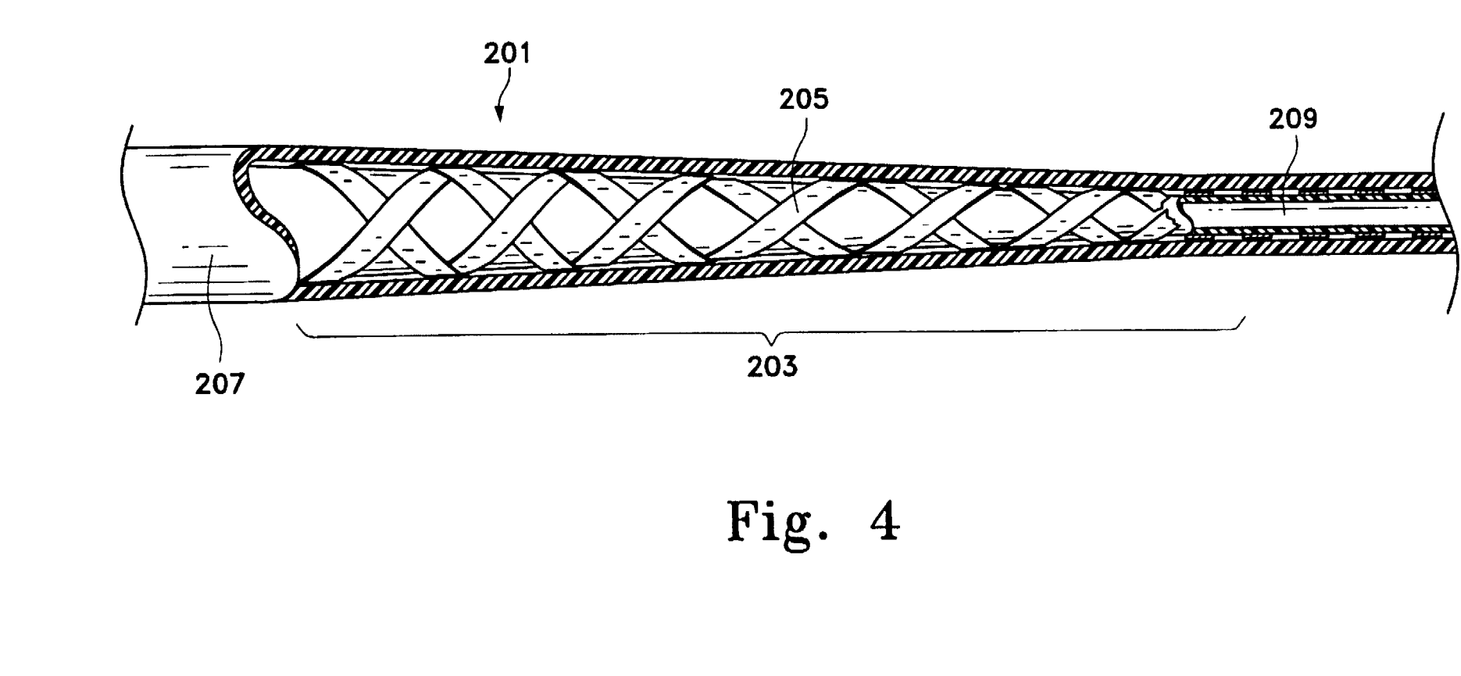

FIG. 4 shows a variation of a catheter section (201) having a tapered section (203). The braid (205) changes its pitch from one end of the tapered section (203) to the other. Judicious choice of polymers allows a smooth transition from the larger adjacent section (207) to the smaller (typically) more distal section (209). The transition section (203) found in FIG. 4 is especially useful in catheters which are used to incorporate high flows of liquid material when the catheter is used for treatment or diagnosis. The smooth transition allows the catheter to be used with ease due to the lower friction through the joint.

The variations shown above have each shown a single-ribbon wind. Single-ribbon winds permit the braid to contain the maximum amount of open area between ribbons in the braid. However, the various catheter sections need not be made with a single ribbon wind.

The invention described herein is intended to encompass multiple-wind braids. That is to say that a plurality of ribbons are placed side-by-side and woven together as shown with the the single ribbon weave above. However, some of the benefits of the invention may be diminished as the density of the ribbons in the catheter section is increased. That is to say that the stiffness of the catheter section substantially increases as the number of ribbons used in a multiple-ribbon weave is increased. The catheter sections shown in the Figures may be combined in a variety of manners to produce a composite catheter assembly. As mentioned above, the typical vascular catheter is made up of a number of sections, typically each more flexible than the section more proximal.

Figure 5:
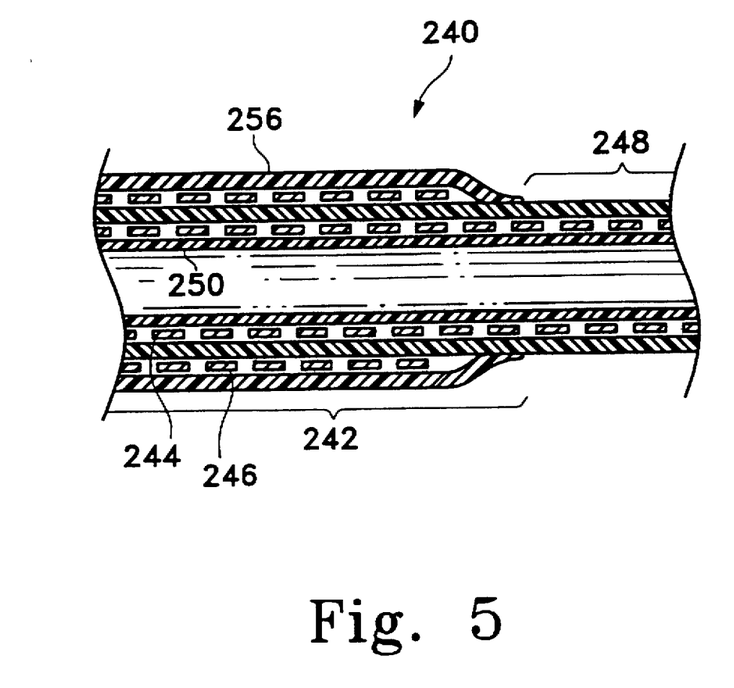
FIGS. 5, 6, and 7 show, in magnified cross-section, various catheters having sections of differing stiffness.
Figure 6:
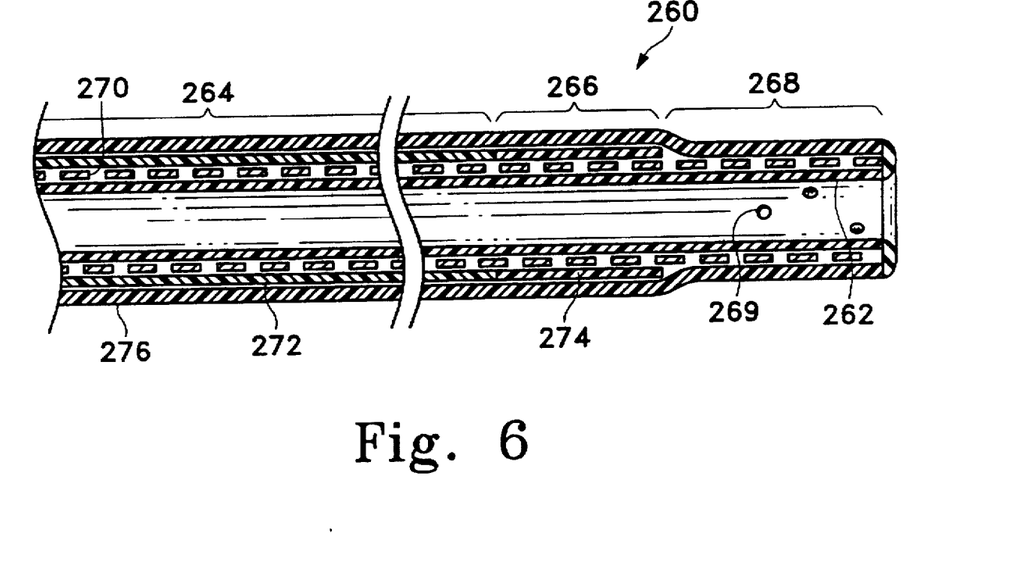
Figure 7:
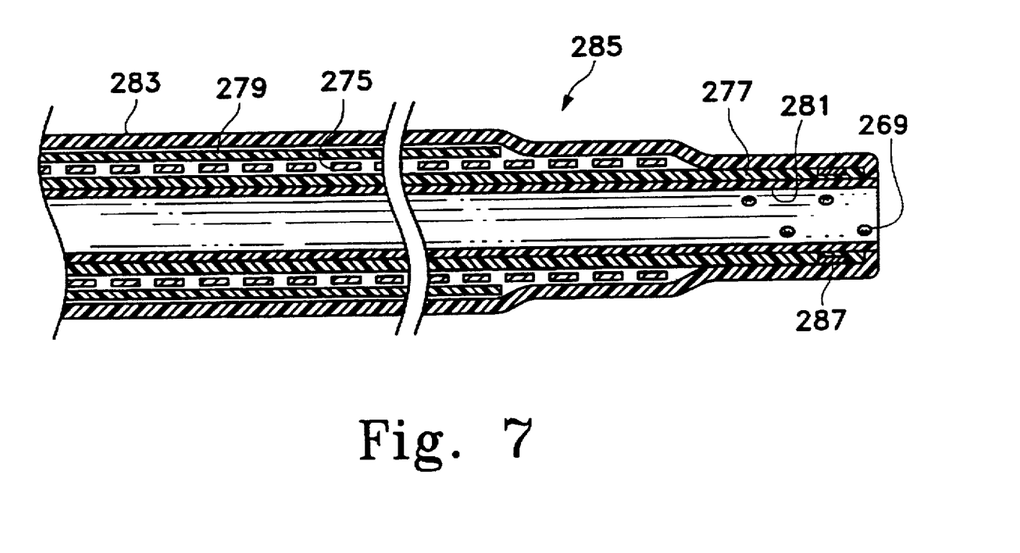

FIGS. 5–7 show various ways to use braided catheter sections in producing a catheter with sections of differing stiffness.

FIG. 5 shows another variation of a catheter assembly made using multiple layers of braided sections. This catheter assembly (240) uses a proximal section (242) made up of a number of layers but including an inner braid (244) and an outer braid (246). The inner braid (244) also extends down into and extends through the length of midsection (248). In this variation, the inner liner member (250) coextends, is coaxial with, and is internal to the inner braid (244). A middle layer of a polymeric tubing (254) extends from the proximal end of the catheter distally. A further outer covering (256) covers braid (246).

Designs such as shown in FIG. 5 is one of exceptional stiffness in the proximal section (242). Although not critical for most neurological applications, such a catheter design has exceptional torque transmission. Such a catheter design may be desirable where a catheter is used for coronary or peripheral access.

A catheter design desirable for peripheral or coronary access is shown in FIG. 6. In this variation, catheter assembly (260) includes a tubing liner (262) which extends throughout the complete catheter assembly (260) from proximal section (264) through midsection (266) to distal section (268). More importantly, the braid (270) also coextends the length of inner liner (262). Differences in flexibility for the respective sections are provided by the use of polymeric tubing members (272) for the proximal section (264) and midsection tubing member (274) for the catheter assembly midsection (266). Various orifices (269) are shown in the distal end section (268) and will be discussed further below. The absence of additional polymeric members other than the outer polymeric covering (276) renders distal section (268) the most flexible.

FIG. 7 shows a preferred variation of the invention in which the braided member (275) is surrounded by an inner polyurethane layer (277) and an upper polyurethane layer (279). The innermost layer (281) is a tubular member comprised of a polyfluorocarbon such as PTFE which preferably has been etched (as discussed above) so to provide a good bond with the adjacent polyurethane layer. The outermost layer (283) is also made of a polyurethane. The distal section contains a number of orifices (269). The section (285) also is shown with a radio-opaque band (287) in the distal end. In such a variation, the various polyurethanes vary in hardness according to their position on the section. For instance, the outermost layer (283) and the upper layer (279) might be one having a Shore 75A–85A hardness; the inner layer (277) might be a Shore 55D polyurethane or the like. Various spacers and adhesives have been omitted from the depiction of the variations to simplify those drawings.

Figure 8:
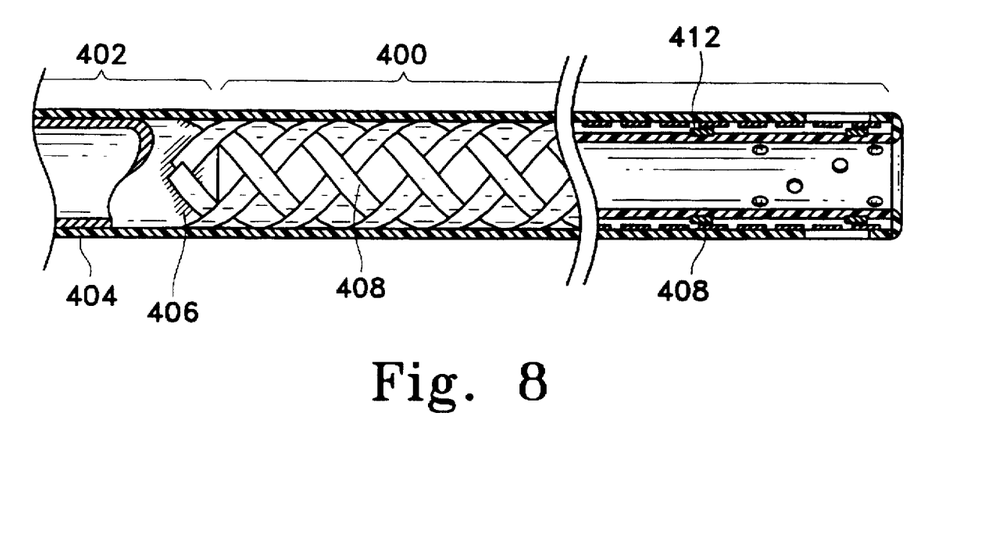
FIG. 8 shows, in magnification, partial cross-sections of the inner portion of a catheter section.

The braid-augmented catheter sections may be used in conjunction with other catheter portions which are more proximal to the individual sections discussed above. FIG. 8, for instance, depicts, in partial cross section, a typical joint as might be found between a more-proximal section comprising metallic tubing (e.g., "hypotube") and a braided more-distal section. In this instance, the more distal-section of the invention is adjacent the more-proximal catheter section of the invention. In particular, the braid (408) in the more-distal section (400) is soldered or welded or otherwise attached (406) to the more-proximal segment (402). Orifices (269) are shown in the distal section. An outer covering (404) such as has been discussed above may be applied to the outer surface of both the moredistal section (400) and the more-proximal segment (402). The outer covering (404) may be a material of suitable flexibility and compatibility such as a polyurethane or low density polyethylene and obviously may be covered or coated with a lubricious polymeric material such as a hydrophilic polymer material, e.g., one containing polyvinylpyrrolidone. The more-distal catheter section (400), as well as the stiffer more-proximal section, may include a lubricious inner layer (not shown), e.g., a Teflon or similar, as has been discussed above.

Figure 9:
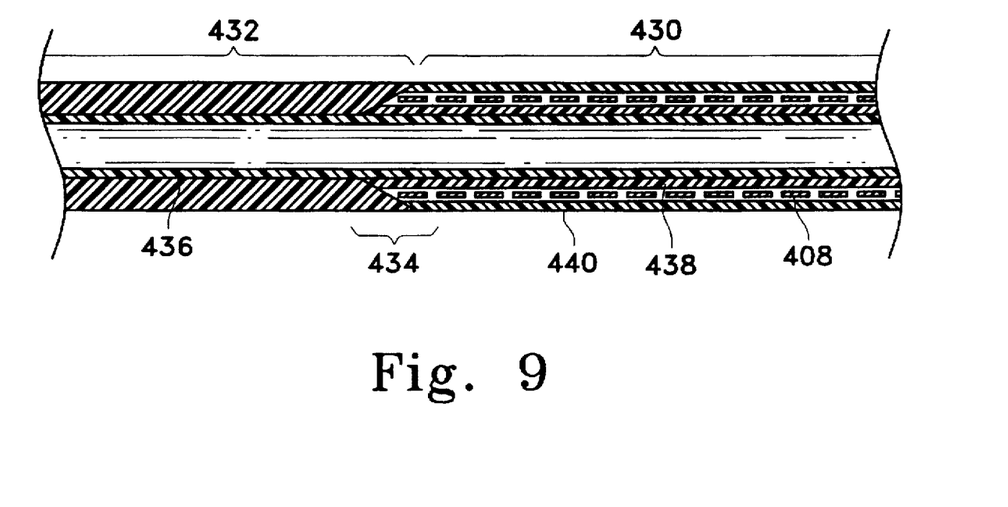
FIG. 9 shows, in magnified cross-section, a catheter having sections of differing stiffness.

FIG. 9 depicts in partial cross-section another variation of the invention in which a more-distal segment (430) is attached to the more-proximal segment (432) via a conical or scarf joint (434). In this variation the depicted sections have a common lubricious inner layer (436), e.g., a Teflon or similar, as has been discussed above. This inner layer (436) is optional and need not be found in each such segment. Nevertheless, the inner layer provides for a number of benefits: it may form the cover for a mandrel upon which the adjacent layer (438) and then upon which the braid (408) may be wound or braided. As noted, the inner layer may be omitted, particularly in the more proximal region (432) since the majority of materials which are suitable for the more proximal section are very "hard" and suitably slippery for passage of guidewires and the like. The more-proximal section (432) may be a simple tubular member comprising unfilled, filled, or fiber-reinforced, tough, polymeric materials preferably having high flexural moduli. Examples generically include polyamides (Nylons 6, 66, 69, 610, 612, 46, 11, and aromatic polyamides such as supplied by DuPont, Huls, etc.), polyamide-polyimides (such as those supplied by Amoco Performance Products), polyimides (both thermoset and thermoplastic), polycarbonates, LCP's, acetals (such as Delrin), and (preferably) stiffer polyolefins such as polypropylene or high density polyethylene, etc.

To integrate the more proximal region (432) of the catheter assembly with materials found in adjacent regions, the choice of materials for the proximal section is desirably a polyamide which is melt-miscible with a polymeric component found in the next more distal segment. In this preferred instance, the more distal region (430) may(for instance) have a covering (440) of polyurethane, a block copolymer of a polyether and a polyamide (e.g., a PEBAX), or a low durometer Nylon. Such polymers are melt miscible with the Nylon of the more distal section (432). The outer covering (440) and the more distal section (432) may be covered or coated with a lubricious polymeric material such as a hydrophilic polymer material. It is also highly desirable to choose a translucent or transparent polymer for this section to assist the physician in use of the catheter assembly.

Figure 10:
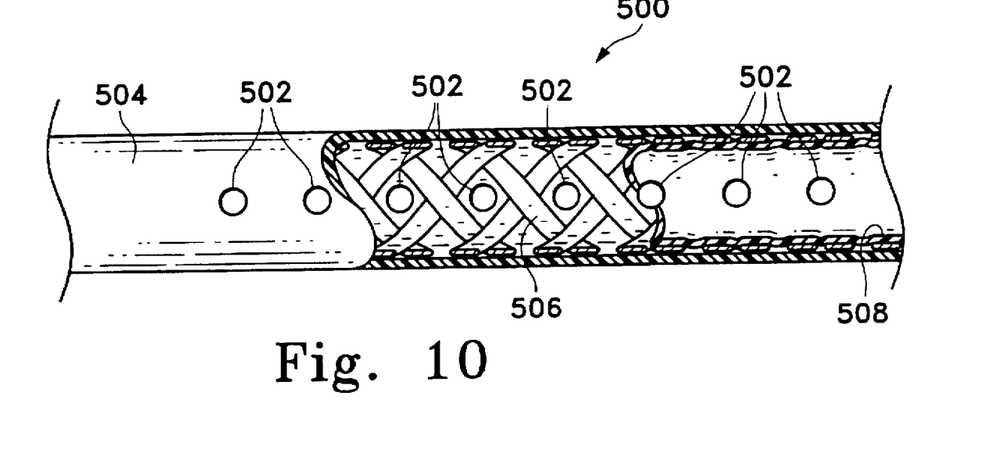
FIG. 10 shows, in magnified, partial cross-section, an infusion catheter section made according to this invention.

FIG. 10 shows in partial impartial cross-section of highly desirable variation of a catheter (500) made according to this invention. The catheter section (500) shown in FIG. 10 (along with FIGS. 11, 12, and 13) are typically used as a distal-most section of a catheter assembly as discussed above. FIG. 10 shows the relationship of a number of orifices (502) as they pass through the outer polymeric layer (504) through braid (506) and finally through interpolymeric layer (508). In particular, it should be noted that the ribbons of braid (506) are wound with sufficient space between them that the orifices (502) may be placed in the interstices between coil ribbon turns. The various orifices (502) shown in FIG. 10 are depicted as having generally the same diameter and are a straight line. The invention is not so limited however. Other combinations of orifice size and configuration are acceptable and in some cases are desirable. As has been noted above, these orifices (502) are used to allow passage of therapeutic and diagnostic fluids from the interior lumen of the catheter section into the region outside the catheter section. In many catheters having distally placed orifices such as are found here, there is a tendency to kink using the orifices as the center of those kinking regions. In the structure such as is shown in FIG. 10, the braid (506) significantly lessens the tendency of the catheter section (500) to kink in any way and particularly lessen the problem of kinking around the orifices (502).

Figure 11:
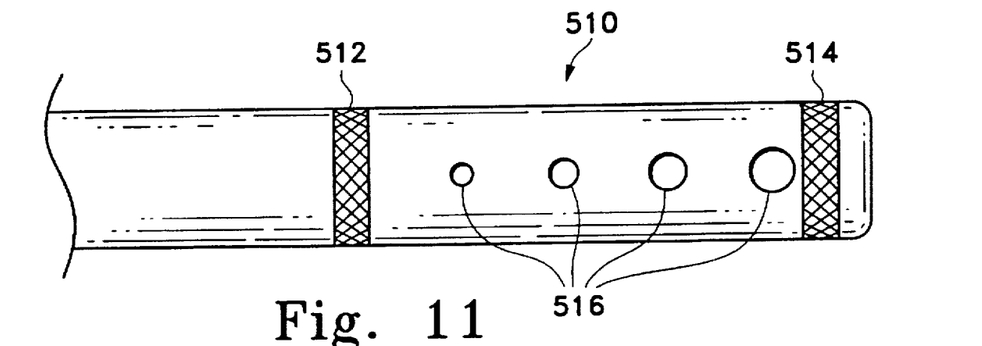
FIGS. 11 and 12 show magnified side views of catheter sections made according to the invention.

FIG. 11 shows an outside view of a catheter distal tip (510) and depicts two desirable features of such distal tips made according to the invention. In particular, it shows the use of a proximal radio-opaque band (512) and a distal radio-opaque band (514). Use of such bands bracketing the region in which the various orifices (516) is found allows the tending physician to more specifically place the region in the desired treatment or diagnostic site.

Further, the series of orifices 516 shown in catheter section (510) is depicted in sizes which are not the same. This, as noted above, is a feature of this invention which may be used in a variety ways. The depiction shown in FIG. 11, the diameter of the orifice (516) which is most distal has the largest diameter. The smallest diameter orifice is most proximal. In this way, fluids which are introduced through the lumen of the catheter section (510) is distributed into the region to be treated in a fashion which is more even than would be the case with orifices (502) shown in FIG. 10. This is a problem in ordinary hydrodynamics easily solved by one of ordinary skill in the flow art.

Figure 12:
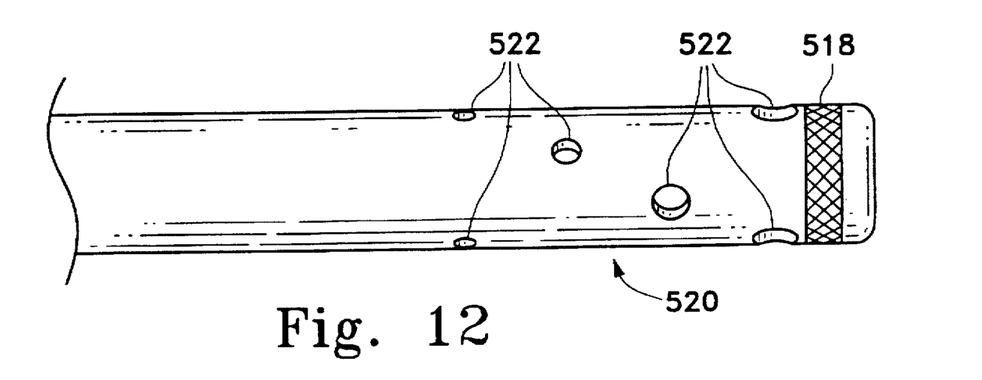

FIG. 12 also depicts a variation of the inventive section having two features of significance to the invention. In this instance, only a single radio-opaque bank (518) is shown in catheter section (520). In this instance, the various orifices (522) are found in a variety of sizes and are arranged in a generally spiral fashion about the exterior of the catheter section surface (520). This allows placement of the fluid within the catheter in a spray pattern generally surrounding the exterior of catheter section (520).

Figure 13:
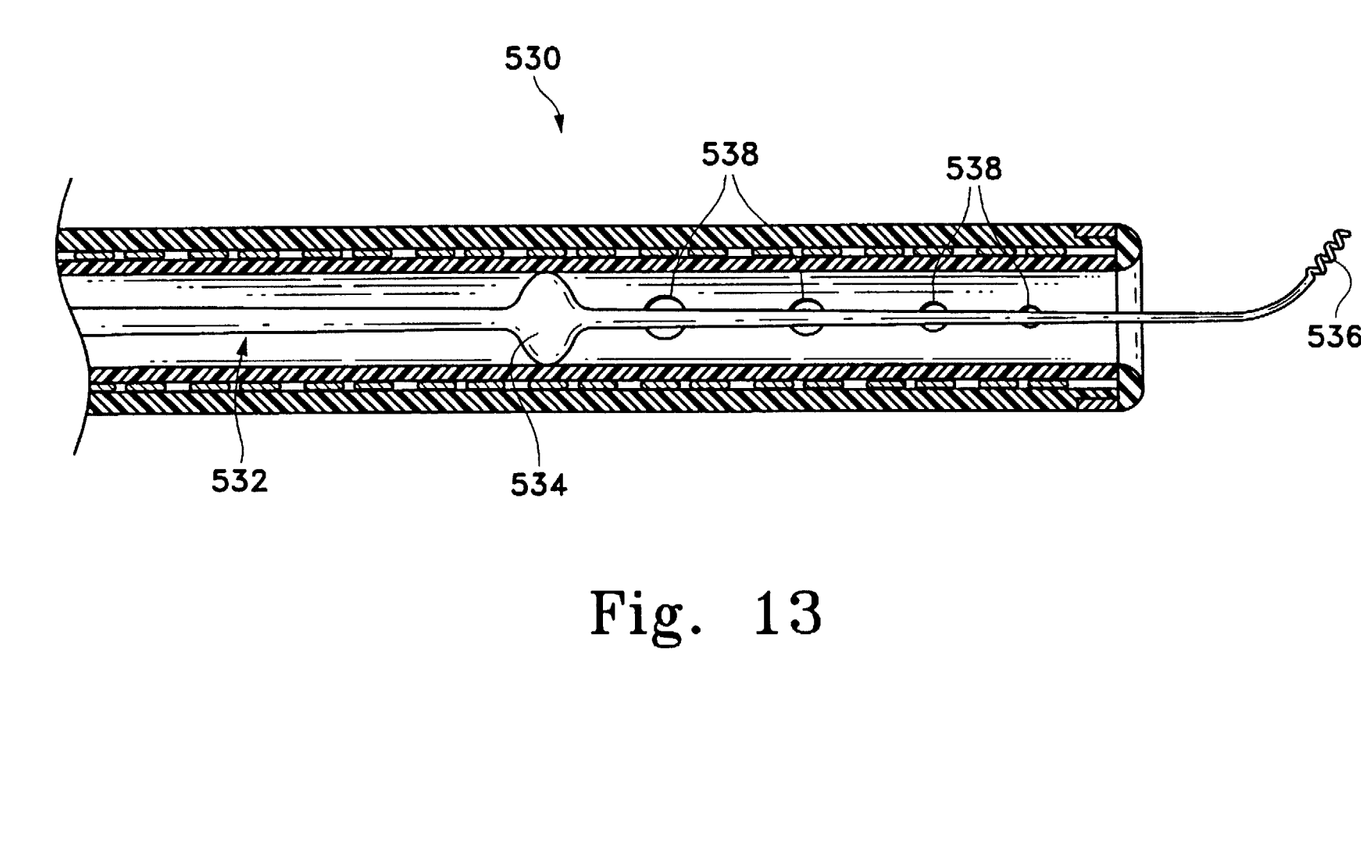
FIG. 13 shows, in cross-section, a combination of a catheter section made according to this invention and an attendant valved guidewire made according to this invention.

FIG. 13 shows, in combination, catheter section (530) in combination with a guidewire assembly (532) having a valving region (534). Guidewire assembly (532) is also shown with a leading coil (536) which may be radio-opaque and may be formable by the user. A number of orifices (536) are also shown in the wall of the catheter. The valving section (534) of guidewire assembly (532) is used in such a way that it may allow exit of fluids from the interior lumen of catheter section (530) in selected regions through a number of the orifices (536). In this way, the guidewire assembly (532) is simply used as a controlling device to further enhance control of the fluid flow of therapeutic or diagnostic materials into the selected body opening or site.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that those claims cover those variations as well.

We claim as our invention:

1. A catheter section for infusion of fluids comprising:
   an elongate tubular member having an outer surface, a proximal end, a distal end, and a passageway defining an inner lumen extending between those proximal and distal ends, said elongate tubular member comprising
   a.) a braid member extending along at least a portion of the distance between the proximal end and the distal end, said braid member being woven of a plurality of ribbons wound and woven to provide for interstices between said ribbons, at least a majority of which ribbons comprise a super-elastic alloy,
   b.) at least one polymeric inner lining member interior to said braid member defining said inner lumen, and
   c.) at least one polymeric outer covering member exterior to said braid member defining said outer surface, and
   wherein the elongate tubular member has a plurality of orifices extending from said inner lumen, through said interstices between said ribbons without contacting said ribbons, and to said outer surface.

2. The catheter section of claim 1 wherein said at least one polymeric inner lining member interior to said braid member comprises a polyfluorocarbon.

3. The catheter section of claim 2 wherein said at least one polymeric inner lining member interior to said braid member comprises polytetrafluoroethylene.

4. The catheter section of claim 3 wherein said at least one polymeric inner lining member interior to said braid member further comprises a polyurethane lining member between said braid member and said polytetrafluoroethylene.

5. The catheter section of claim 4 wherein said polyurethane lining member interior to said braid member is in contact with said polytetrafluoroethylene.

6. The catheter section of claim 3 wherein said elongate tubular member has a distal and a proximal end and said polytetrafluoroethylene extends between said distal end and proximal end.

7. The catheter section of claim 3 wherein said elongate tubular member has a distal and a proximal end and said braid extends between said distal end and proximal end.

8. The catheter section of claim 1 wherein the super-elastic alloy comprises a nickel-titanium alloy further containing an alloying member selected from the group consisting of vanadium, chromium, manganese, iron, and cobalt.

9. The catheter section of claim 8 wherein the alloying member is selected from the group consisting of chromium and iron.

10. The catheter section of claim 1 wherein the at least one polymeric inner lining member and said at least one polymeric outer covering member independently comprise polymers selected from the group consisting of polyimides, polyamides, polyesters, polyethylene, polypropylene, polyvinylchloride, polyfluorocarbons polyurethanes, polysulfones, and their mixtures, alloys, blends, copolymers, and block copolymers.

11. The catheter section of claim 1 wherein the superelastic alloy comprises a nickel-titanium alloy.

12. The catheter section of claim 1 wherein a minority of the braid member ribbons comprise stainless steel.

13. The catheter section of claim 1 wherein a minority of the braid member ribbons comprise a member selected from the group consisting of platinum, tungsten, gold, and their mixtures and alloys.

14. The catheter section of claim 1 wherein the at least one inner lining member and said at least one outer covering member are radiation sterilizable without substantial degradation of physical attributes.

15. The catheter section of claim 1 wherein the braid member has a braid pitch and a braid axis and that braid pitch is constant along the axis of the braid member.

16. The catheter section of claim 1 wherein the braid member has a braid pitch and a braid axis and that braid pitch is not constant along the braid axis.

17. The catheter section of claim 1 wherein the braid member has an outer diameter and a braid axis and that outer diameter is not constant along the braid axis.

18. The catheter section of claim 1 wherein the braid member has an outer diameter and a braid axis and that outer diameter tapers along the braid axis.

19. The catheter section of claim 1 where the braid member ribbons have a thickness between 0.5 mil and 3.5 mil and a width between 2.5 and 12.0 mil.

20. The catheter section of claim 1 wherein at least one of a5.) the at least one inner lining member and b.) the at least one outer covering member contains a radio-opacifier.

21. The catheter section of claim 1 further comprising more than one braid member located coaxially with respect to each other.

22. The catheter section of claim 1 wherein said elongate tubular member has a critical bend diameter of no more than 3.0 mm.

23. The catheter section of claim 1 wherein said elongate tubular member has a critical bend diameter of no more than 2.0 mm.

24. The catheter section of claim 1 wherein said elongate tubular member has a critical bend diameter of no more than 1.0 mm.

25. The catheter section of claim 1 wherein the orifices have differing diameters.

26. The catheter section of claim 1 wherein the orifices are spirally arranged.

27. The catheter section of claim 1 wherein the orifices are spirally arranged in order of diameter, the larger diameter being nearest the distal end of the elongate tubular member.

* * * * *